United States Patent
Shalaby et al.

(10) Patent No.: US 9,402,932 B2
(45) Date of Patent: *Aug. 2, 2016

(54) IN SITU-FORMED BIOACTIVE TISSUE ADHERENT FILMS OF ABSORBABLE CRYSTALLIZABLE POLYMERS

(71) Applicant: Poly-Med, Inc., Anderson, SC (US)

(72) Inventors: Shalaby W. Shalaby, Anderson, SC (US); Joel T. Corbett, Seneca, SC (US); Jason Olbrich, Clemson, SC (US)

(73) Assignee: Poly-Med, Inc., Anderson, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/480,732

(22) Filed: Sep. 9, 2014

(65) Prior Publication Data

US 2014/0377211 A1 Dec. 25, 2014

Related U.S. Application Data

(63) Continuation of application No. 12/931,279, filed on Jan. 29, 2011, now Pat. No. 8,828,425.

(60) Provisional application No. 61/337,295, filed on Feb. 2, 2010.

(51) Int. Cl.
*A61L 26/00* (2006.01)
*A61F 13/00* (2006.01)
*A61L 15/26* (2006.01)
*A61K 9/00* (2006.01)
*A61K 9/70* (2006.01)
*A61K 31/4196* (2006.01)
*A61K 47/34* (2006.01)

(52) U.S. Cl.
CPC .............. *A61L 26/0076* (2013.01); *A61F 13/00* (2013.01); *A61K 9/0014* (2013.01); *A61K 9/0017* (2013.01); *A61K 9/7015* (2013.01); *A61K 31/4196* (2013.01); *A61K 47/34* (2013.01); *A61L 15/26* (2013.01); *A61L 26/009* (2013.01); *A61L 26/0019* (2013.01); *A61L 26/0066* (2013.01); *A61L 2300/404* (2013.01); *A61L 2300/602* (2013.01); *A61L 2300/604* (2013.01); *A61L 2430/34* (2013.01)

(58) Field of Classification Search
None
See application file for complete search history.

(56) References Cited

U.S. PATENT DOCUMENTS

| | | | | |
|---|---|---|---|---|
| 2,972,545 | A * | 2/1961 | Briskin | 424/45 |
| 4,987,893 | A * | 1/1991 | Salamone | A61L 15/26 128/DIG. 21 |
| 5,486,593 | A | 1/1996 | Tang et al. | |
| 7,348,364 | B2 | 3/2008 | Shalaby | |
| 8,828,425 | B2 * | 9/2014 | Shalaby | A61K 47/34 424/447 |
| 8,951,552 | B2 * | 2/2015 | Shalaby et al. | 424/447 |
| 2004/0013629 | A1 * | 1/2004 | Andolino Brandt | A61K 9/7015 424/70.16 |
| 2004/0109892 | A1 * | 6/2004 | Shalaby | A61K 47/482 424/468 |
| 2004/0242770 | A1 | 12/2004 | Feldstein et al. | |
| 2006/0025516 | A1 | 2/2006 | Shalaby et al. | |

* cited by examiner

*Primary Examiner* — Theodore R West

(57) ABSTRACT

An in situ film-forming sprayable methyl acetate-based solution of at least one absorbable, low-crystallinity, segmented copolymer contains at least one bioactive agent, which exhibits antimicrobial, anti-inflammatory, antiviral, anesthetic, hemostatic, and/or antineoplastic activity. The absorbable polymers can be a polyaxial copolyester, polyether-ester and polyether-ester urethane and the bioactive solution thereof can be applied onto animal and human skin or accessible body cavities to prevent or treat one or more disorder susceptible to the bioactive agent therein.

9 Claims, No Drawings

IN SITU-FORMED BIOACTIVE TISSUE ADHERENT FILMS OF ABSORBABLE CRYSTALLIZABLE POLYMERS

CROSS REFERENCE OF RELATED APPLICATION

The present application claims priority to provisional application U.S. Ser. No. 61/337,295, filed Feb. 1, 2010.

FIELD OF THE INVENTION

This invention is directed to an in situ-formed bioactive tissue adherent compliant film produced by spraying a methyl acetate solution of an absorbable crystallizable polymer containing at least one soluble or microdispersed bioactive agent. Depending on the application site, the film composition is designed to display a one hundred to six hundred percent elongation and can be applied on animal or human skin and walls of accessible body cavities for controlled release of a variety of bioactive agents including antifungals and antibacterials to treat or prevent the respective infections.

BACKGROUND OF THE INVENTION

Interest in developing a practical form of bandages or covers that are formed in situ on a wound by spraying a solution or dispersion of a polymer(s) in a liquid carrier dates back to the early 1970s, when for instance the preparation of a spray-on bandage was described in U.S. Pat. No. 3,577,516. In the latter the inventors outlined the requirements for a fully acceptable spray-on bandage to include the following:
 (1) It protects the wound from air borne bacteria and dirt.
 (2) It has moisture vapor permeability sufficient to prevent accumulation of aqueous fluid under the bandage.
 (3) It must be non-toxic and non-irritating to the skin.
 (4) It should not adhere to the wound area or permit infiltration by regenerating tissue.
 (5) It should not cause a burning or stinging sensation when applied.
 (6) It should not be water soluble or rendered tacky by contact with water to avoid dirt accumulation.
 (7) It should be readily removable when desired.

Those inventors also noted that prior art spray-on products suffer from a number of disadvantages with respect to the above criteria. Thus prior art materials having the desired moisture vapor permeability coupled with water resistance must be applied as a spray from alcohol or similar solvent solution which causes a strong burning sensation in the wound area. Hence, the objective of U.S. Pat. No. 3,577,516 was to develop a spray-on bandage having all seven of the above set forth desirable characteristics while avoiding the disadvantages of prior art spray-on bandages. More specifically U.S. Pat. No. 3,577,516 dealt primarily with a method of forming a powdery bandage in situ on skin having a wound therein which is readily removable therefrom after soaking, the improvement comprising the steps of (a) applying, as a powder, a hydrophilic water insoluble hydroxyl or lower alkoxy lower alkyl acrylate or methacrylate polymer or a copolymer of 20 to 70% of a lower acrylate or methacrylate and 80 to 30% of acrylamide, methacrylamide, N-lower alkyl acrylamide or methacrylamide, or N-vinylpyrrolidone as a powder and (b) applying, simultaneous or in succession, a high boiling liquid plasticizer or solvent therefor which does not cause a burning or stinging sensation when applied on the skin resulting from adherence of the powder to the wound area wet with the non-stinging plasticizer solvent thereby covering said wound wherein the polymer powder and plasticizer are sprayed from separate containers in succession, or wherein the polymer powder and plasticizer are simultaneously sprayed from separate chambers in a single container, or wherein the polymer powder and plasticizer are sprayed simultaneously from the same chamber in a single container, the plasticizer and polymer powder being kept separate by the propellant which prevents salvation and agglomeration of the polymer powder by the plasticizer, wherein the polymer is in finely divided form, substantially uncrosslinked and has a moisture vapor permeability of at least 200 grams/sq. meter/24 hours/mil and the application is accomplished by spraying as an aerosol with the aid of a propellant.

Extension of the in situ-forming film technology was described in U.S. Pat. No. 6,958,154 and dealt with a spray-on bandage and drug delivery system. This provided the so called patch-in-a-bottle technology in which a fluid composition, e.g., an aerosol spray, is applied onto a surface as a fluid, but then dries to form a covering element, such as a patch, having a tack-free outer surface covering an underlying adhesive that helps to adhere the patch to the substrate. The fluid compositions have a unique chemical formulation that allows such composite patches to form in situ. Specifically, the fluid compositions include a tacky component, such as an adhesive, and a film-forming, non-tacky component. The non-tacky and tacky components are selected to be immiscible with each other so that the components undergo phase separation as the fluid composition dries. Accordingly, U.S. Pat. No. 6,958,154 claimed a fluid composition suitable for in situ forming and adhering to a touch-dry, non-tacky covering element onto a surface, comprising:
 (a) an effective amount of a tacky component such that the formed covering element adheres to the surface, wherein the tacky component comprises a pressure sensitive adhesive comprising a methacrylate polymer, further wherein the methacrylate polymer is a copolymer of monomers comprising about 40 to about 100 weight percent of an alkyl methacrylate and 0 to about 60 weight percent of a free radically 20 copolymerizable monomer;
 (b) a film-forming, non-tacky component, wherein said film-forming; non-tacky component comprises at least one low surface energy, surface seeking moiety, wherein said film-forming, non-tacky component is incompatible with the tacky component, and wherein the film-forming, non-tacky component is present in an effective amount such that upon application it undergoes phase separation from the tacky component such that an outer surface of the in situ formed covering element is non-tacky when the covering element is touch dry; and
 (c) a sufficient amount of at least one volatile solvent such that the fluid composition has a coatable viscosity allowing the fluid composition to be coated onto said surface.

In a series of disclosures (U.S. Pat. No. 4,987,893, U.S. Pat. No. 5,103,812, and U.S. patent application Ser. No. 11/465, 237), conformable solvent-based bandage and coating materials were discussed by the inventors, specifically, combinations of alky siloxy siloxane-containing polymers admixed with liquid polydimethylsiloxanes are excellent non-stinging, non-irritating liquid coating material for forming films, which act as conformable bandages adhering to and protecting nails, skin and mucous membrane wounds from abrasion, contamination, and desiccation, while stopping pain from exposed nerve ends and allowing body fluid evaporation U.S. Pat. Nos. 4,987,893 and 5,103,812). In one primary claim (U.S. Pat. No. 4,987,893) the inventors described a liquid polymer-containing bandage material comprising 1 to 40 weight percent siloxane containing polymer, 59.9 to 98.9 weight percent volatile polydimethylsiloxane liquid, and 0.1 to 10 weight percent polar liquid; said bandage material being substantially non-stinging and film forming at room temperature to form an adherent conformable moisture vapor permeable bandage directly on a user. In a second major claim (U.S. Pat. No. 5,103,812), the inventors described a liquid polymer-containing coating material comprising from 1 to 40 weight percent siloxane containing polymer, 59.9 to 98.9 weight percent volatile polydimethylsiloxane, and 0.1 to 10 weight percent polar liquid; said coating material being substantially non-stinging and film forming at room temperature to form an adherent conformable moisture 35 vapor permeable coating directly on a user, wherein said siloxane-containing polymer is soluble in hexamethyldisiloxane and comprises a monomer component that is a silane derivative, a monomer component that when provided as a homopolymer would prepare a hard polymer, and a monomer component that, when provided as a homopolymer would prepare a soft polymer. In a subsequent disclosure, those inventors described liquid hemostatic coating materials that comprise a cyanoacrylate monomer and a solvent system comprising a volatile, non-reactive liquid that is non-stinging and non-irritating to a user. The material forms a coating or bandage in the form of a film that when applied and adhered to a surface or to the skin of a user inhibits the application surface from adhering to another surface (U.S. patent application Ser. No. 11/465,237). Specifically, the primary claims described a liquid coating material comprising about 0.1 to about 99.9 weight percent polymerizable cyanoacrylate monomer and about 0.1 to about 99.9 weight percent non-stinging, non-irritating, volatile, non-reactive liquid; said coating material being hemostatic on bloody, moist and non-moist surfaces to form an adherent, conformable polymer coating, which adherent, conformable coating does not adhere to a second surface, wherein the liquid coating comprises about 0.01 to about 99.5 percent by weight siloxysilane-containing polymer, about 0.1 to about 99.5% by weight polymerizable cyanoacrylate monomer and about 0.5 to about 99.9% by weight non-stinging, non-irritating, volatile hydrophobic liquid; said coating materials being film-forming on bloody, moist and non-moist surfaces to form an adherent, conformable, moisture vapor permeable, hemostatic, interpenetrating polymer coating, which coating does not adhere to a second surface, and wherein said polymerizable cyanoacrylate monomer component comprises alpha-cyanoacrylates.

Growing interest in exploring new biomedical applications of the absorbable polymer technology coupled with existing experience with in-situ forming non-absorbable film as discussed above directed the attention of Tipton et al. (U.S. Pat. Nos. 5,632,727 and 5,792,469) to the preparation of a biodegradable film dressing with or without additional therapeutic agents, an apparatus for spray delivery and a method for formation of the film dressing on a human or animal tissue. The film dressing is formed from a liquid composition of at least one biodegradable/bioerodible thermoplastic polymer in a pharmaceutically acceptable solvent. The spray apparatus includes a vessel containing the liquid composition with a dispensing means. The film is formed by dispensing, preferably by spraying, the liquid composition onto a tissue site and contacting the liquid composition with an aqueous-based fluid to coagulate or solidify the film onto the human or animal tissue. The biodegradable film can be used to protect and to promote healing of injured tissue and/or to deliver biologically active agents. The primary claims of these disclosures deal with a biodegradable microporous film dressing comprised of a skin and a core portion, the skin portion having pores with a smaller diameter than pores of the core portion; wherein the film dressing is formed by contacting a composition comprising a biodegradable thermoplastic polymer that is insoluble in aqueous or body fluids, and an organic solvent that is soluble in aqueous or body fluids, with an aqueous or body fluid whereupon the composition coagulates or solidifies to form the microporous film dressing, wherein the film dressing is formed by administering the composition onto tissue, and the core portion of the film dressing is orientated under the skin portion and in contact with the tissue, and further wherein the film dressing is formed by administering the composition onto a tissue and the skin portion of the film dressing is orientated under the core portion and in contact with the tissue. Meanwhile, the biodegradable thermoplastic polymer is selected from the group consisting of polylactides, polyglycolides, polycaprolactones, polyethylene glycols, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(amino acids), poly (methyl vinyl ether) and copolymers, terpolymers, and combinations thereof. The solvent used in dissolving the polymers included N-methyl-2-pyrrolidone, 2-pyrrolidone, acetone, acetic acid, ethyl acetate, ethyl lactate, methyl acetate, methyl ethyl ketone, dimethylformamide, dimethylsulfoxide, dimethyl sulfone, tetrahydrofuran, caprolactam, decylmethylsulfoxide, oleic acid, propylene carbonate, N,N-diethyl-m-toluamide, and 1-dodecylazacycloheptan-2-one, and mixtures thereof. A second primary claim made by those inventors dealt with a liquid composition suitable for forming an in situ biodegradable film dressing on a human or animal tissue, comprising: a liquid formulation of a biodegradable thermoplastic polymer that is insoluble in aqueous or body fluids and an organic solvent that is soluble in aqueous or body fluids; wherein the composition comprises about 0.01-2 g polymer per mL solvent, and has a viscosity of about 45 0.1-2000 cps which effectively allows for aerosolization, and wherein the amount and molecular weight of said polymer is such that the composition is capable of coagulating or solidifying to form a film dressing upon contact with an aqueous or based fluid. Meanwhile, (1) the solvent is a liquid aerosol propellant that can be selected from the group consisting of trichloromonofluoromethane, dichlorodifluoromethane, dichloromonofluoromethane, 2-tetrafluoroethane, 1,1dichloro-1,2,2-tetrafluoroethane, 1-chloro-1,1difluoroethane, 1,1-difluoroethane, octofluorocyclobutane, propane, isobutane, N-butane, and mixtures thereof and (2) "biodegradable thermoplastic polymer is selected from the group consisting of polylactides, polyglycolides, polycaprolactones, polyethylene glycols, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(amino acids), poly (methyl vinyl ether), and copolymers, terpolymers, and combinations thereof.

The use of a natural gum resin as a carrier for topical application of pharmacologically active agents was the subject of U.S. Pat. No. 6,899,897, which described a biological dressing for treatment of a dermatological disease comprised of a gum resin, a topically acceptable volatile solvent, and a pharmacologically active agent. The gum resin is present in a suitable amount that the composition, when the solvent evaporates, will dry to form a solid coating that sticks to the skin or mucosal membrane to which the composition is applied and maintain the pharmacologically active agent over a sustained period of time in contact with sites on the skin or mucosal membranes exhibiting symptoms of the disease. Methods are provided for treating symptoms of dermatological diseases with such a pharmacological composition. Biological dressings including tincture of benzoin and clotriconazole are shown to be efficacious for the long-term amelioration of symptoms of athlete's foot.

The primary claims of U.S. Pat. No. 6,899,897 dealt with a pharmacological composition comprising: (1) a gum resin, wherein said gum resin comprises benzoin; (1) at least one topically acceptable pharmacologically active agent other than said gum resin that is effective as a treatment for ameliorating symptoms of a disease of skin or a mucous membrane of a mammal wherein said pharmacologically active gent can remain in contact with said skin or said mucous membrane greater than 6 hours without toxic effects to said mammal; and (3) a topically acceptable volatile solvent for said gum resin and said pharmacologically active agent, wherein said topical acceptable volatile solvent is ethanol and the pharmacological active agent is the antimicrobial agent, clotriconazole.

All patents and patent applications noted in this specification are indicative of the level of skill of those skilled in the art to which the instant invention pertains. However, none of the prior art disclosures dealt with uniquely tailored in situ-formed bioactive tissue adherent films based, specifically, on absorbable crystallizable polymers in a non-irritating, highly volatile organic solvent to ensure optimum applicability, performance as a flexible tissue-adherant, conforming and stretchable protective cover that is also capable of a timely delivery of its drug payload and undergoing biodegradation thereafter. This and the availability of proprietary absorbable polymers in our laboratory that can be processed towards meeting the requirements of such film provided an incentive to pursue the study subject of the instant invention.

SUMMARY OF THE INVENTION

This invention deals in general with an in situ film-forming, sprayable methyl acetate-based solution of at least one absorbable, low-crystallinity, segmented copolymer comprising at least one bioactive agent selected from the group exhibiting antimicrobial, anesthetic, antiviral, anti-inflammatory, hemostatic, and antineoplastic activities, wherein the methyl acetate represents about a hundred weight percent of the solvent component of the methyl acetate-based solution, and wherein said solution can be sprayed on animal or human skin and accessible body cavities to form an adherent, flexible, conformable, stretchable, dimensionally stable film with tack-free outer surface and when tested in the tensile mode, exhibits an elongation of 100 to 600 percent, tensile strength of 3-10 MPa and a tensile modulus of 5-20 MPa, and further wherein the copolymer represents 0.1 to 20 weight percent of the solution.

Another aspect of this invention deals with an in situ film-forming, sprayable methyl acetate-based solution of at least one absorbable, low-crystallinity, segmented copolymer comprising at least one bioactive agent selected from the group exhibiting antimicrobial, anesthetic, antiviral, anti-inflammatory, hemostatic, and antineoplastic activities, wherein the methyl acetate represents about a hundred weight percent of the solvent component of the methyl acetate-based solution, and wherein the at least one absorbable low crystallinity segment copolymer exhibits a heat of fusion ($\Delta H_f$) of 1 to 20 J/g and is selected from the group consisting of polyaxial copolyesters, polyether-esters and polyether-ester-urethanes, and further wherein the at least one bioactive agent wherein said agent represents 0.1 to 15 weight percent of the copolymer and is in said solution as a soluble entity or partially soluble microparticles. More specifically, (a) the polyaxial copolyester is derived from at least two cyclic monomers selected from the group consisting of p-dioxanone, 1,5-dioxapan-2-one, glycolide, l-lactide, ε-caprolactone, trimethylene carbonate and a morpholinedione; (b) the polyether-ester is an end-grafted product of a polyethylene glycol and at least one monomer selected from the group of p-dioxanone, 1,5-dioxapan-2-one, glycolide, l-lactide, ε-caprolactone, trimethylene carbonate and a morpholinedione; (c) the polyether-ester urethane is an end-grafted product of a polyethylene glycol and at least one monomer selected from the group consisting of p-dioxanone, 1,5-dioxapan-2-one, glycolide, l-lactide, ε-caprolactone, trimethylene carbonate and a morpholinedione, the end-grafted product is further interlinked with an aliphatic diisocyanate selected from the group consisting of 1,4-butane, 1,6-hexane, and a lysine diisocyanate.

Yet another aspect of this invention deals with an in situ film-forming, sprayable methyl acetate-based solution of at least one absorbable, low-crystallinity, segmented copolymer comprising at least one bioactive agent selected from the group exhibiting antimicrobial, anesthetic, antiviral, anti-inflammatory, hemostatic, and antineoplastic activities, wherein the methyl acetate represents about a hundred weight percent of the solvent component of the methyl acetate-based solution, and wherein the at least one absorbable low crystallinity segment copolymer exhibits a heat of fusion ($\Delta H_f$) of 1 to 20 J/g and is selected from the group consisting of polyaxial copolyesters, polyether-esters and polyether-ester-urethanes, and further wherein the at least one bioactive agent wherein said agent represents 0.1 to 15 weight percent of the copolymer and is in said solution as a soluble entity or partially soluble microparticles. More specifically, the at least one bioactive agent is selected from the group consisting of miconazole, ketoconazole, metronidazole, curcumin, capsaicin, lidocaine, benzocaine, 8-hydroxyquinaline, triclosan, and paclitaxel.

From a technological perspective, this invention deals with an in situ film-forming, sprayable methyl acetate-based solution of at least one absorbable, low-crystallinity, segmented copolymer comprising at least one bioactive agent selected from the group exhibiting antimicrobial, anesthetic, antiviral, anti-inflammatory, hemostatic, and antineoplastic activities, and said solution comprising methyl acetate as the major component of the solvent and hexadimethyl disiloxane as a minor component From a clinical perspective, this invention deals with an in situ film-forming, sprayable methyl acetate-based solution of at least one absorbable, low-crystallinity, segmented copolymer comprising at least one bioactive agent selected from the group exhibiting antimicrobial, anesthetic, antiviral, anti-inflammatory, hemostatic, and antineoplastic activities and said solution is useful for treating or preventing at least one of the following fungal infection, bacterial infection, viral infection, acne, pain, and bleeding.

DETAILED DESCRIPTION OF PREFERRED EMBODIMENTS

Since the earliest history, tools for wound protection and repair have been used in progressively different forms. However, significant changes in these tools have taken place in the last 60 to 70 years, where gauzes and adhesive bandages began to share the wound care market with adhesive tapes and more recently the so-called liquid bandages. The latter are classified into two main categories. The first category entails skin protectants and over-the-counter gels and sprays that can shield superficial scrapes as well as large chronic bedsores. The second category encompasses the family of tissue adhesives which are used to cover more serious skin lacerations and yet to be widely used in tissue repair as legitimate replacements for mechanical wound closure devices, such as sutures and staples. Most pertinent to the present invention are the tools of the first category. And the instant invention provides unique transient compositions for tissue protection and treatment of wounds during a finite period of time through using novel in situ-formed bioactive tissue adherent films of absorbable, crystallizable polymers.

The uniqueness of the in situ-formed bioactive films can be illustrated as follows:

1. The film-forming polymers are absorbable in nature and their absorption profiles can be modulated by controlling their chemical composition to permit controlling their effective residence time at the application site.

2. The absorbable film-forming polymers are designed to be soluble in the previously unexpected, useful methyl acetate-based solvent that (a) provides the necessary solvating power of a broad range of difficult-to-dissolve film-forming polymers having a broad range of solubility parameters; (b) is capable of dissolving highly potent drugs with established efficacy in a variety of key indications including the treatment of skin and mucus membrane microbial and viral infections; (c) has a low boiling point and can be easily lead to film formation using a simple sprayer; (d) is non-stinging and has a pleasant odor to permit its use on large tissue areas having variable amounts of nerve endings; (e) is capable of dissolving or effectively dispersing nano- and/or microparticulate sun-screening compounds to allow their use in protecting against sun rays and then are removable at will by wiping with a drug-free solvent in a soft pad; and (f) is water-soluble to allow removal of residual amounts by rinsing with water.

3. The absorbable film-forming polymers are designed to have (a) sufficiently high percentages of ultimate elongation to circumvent breakage upon stretching of the application site; (b) sufficiently low modulus and hence, high compliance to prevent unwanted mechanical incompatibility with application sites such as high-compliance soft skin or mucus membranes; (c) low degrees of crystallinity to provide in-use dimensional stability without compromising the compliance or softness of the film; (d) a high degree of light transmission, in spite of the presence of a crystalline fraction to allow a desirable levels of film transparency—the small size of crystallites, as evidenced by pertinent analytical methods, is responsible for such transparency; (e) a range of solvating capacities and absorption profiles to allow their use as depots for the timely and controlled release of the different bioactive agents therein; and (f) the necessary structure to allow their sterilization by one or a combination of traditional means such as ethylene oxide, gamma radiation, electron beam, and less traditional means such as gas plasma and radiochemical sterilization.

4. The in situ-forming sprayable methyl acetate-based solution of crystallizable polymers loaded with antimicrobial agents can be used as an absorbable barrier/sealent with or without specific antibiotics to be applied on any minor laceration in the setting of wound re-approximation after any major or minor surgery. The aforementioned advantages are as follows:

(1) Off-the-shelf use in the operating room without any timely preparation.

(2) Ease of application as a "sprayed" on film to various sized incisions with 100% coverage given it film forming properties regardless of surface incongruency.

(3) May display "mild adhesive" properties in best used after skin re-approximation with subcuticular closures (i.e. suture placed under skin) (4) Broad use in a variety of surgeries as in abdominal surgery (GI-colorectal, GYN, Urologic), obstetrics (skin closure after C-sections), breast surgery for cancer, vascular surgery where amputations are performed due to peripheral vascular disease, hand surgery, foot (podiatric) surgery, plastic surgery (abdominoplasty, breast reduction or augmentation, and fascial surgery), trauma surgery, and emergent surgery where an infection is apparent (ruptured appendix, small or large bowel perforation, gynecologic infections).

(5) Minimize post-op wound infection and provide a barrier system that will exhibit the necessary compliance or stretch as patient activity level increases without comprising skin healing and repair.

(6) Proprietary formulation may display optimal oxygen transmission to the wound based on the hydrophilic properties that retains moisture.

(7) Provides a protective coating and sealant and minimizes drainage at incision sites when there is excessive edema and inflammation whereby the excess fluid may leak in-between the suture-line or of staple line.

(8) May contain antimicrobial compounds as an adjunct to its protective coating. This is relevant to (a) small or large bowel surgery where bowel contents have entered the surgical field—or in the case of ruptured infectious processes such as appendix, tubo-ovarian abscesses, or in the setting trauma where emergent surgery is needed, and (b) patients with poor wound healing potential such as morbidly obese and/or diabetic patients, as well as patients with peripheral vascular disease.

(9) May contain anti-inflammatory agents to minimize swelling and improve pain control with less need for narcotic use post-operatively.

Further illustrations of the present invention are provided by the following examples:

EXAMPLE 1

Synthesis and Properties of a Typical l-Lactide-based Polyaxial Copolyester (PAX-12)

The polymer was prepared using the general procedure for the synthesis of crystalline, segmented, polyaxial copolyesters as described earlier (U.S. Pat. No. 7,348,364 and U.S. patent application Ser. No. 11/598,427). An amorphous polymeric initiator comprising 35/14/9 (molar) ε-caprolactone/trimethylene carbonate/glycolide was made and end-grafted to form crystalline eng-grafts comprising 42/2 (molar) l-lactide/glycolide to yield a copolyester made of 35/14/34/17 (molar) caprolactone/trimethylene carbonate/l-lactide/glycolide. The polymer was characterized for identity (IR, NMR), molecular weight (in terms of inherent viscosity), and thermal property (DSC). It was shown to have an inherent viscosity of 1.45 dL/g, melting temperature of 109° C., and heat of fusion of 7.4 J/g.

EXAMPLE 2

Film Tensile Properties of Polyaxial Copolyester (PAX-12) from Example 1

A sample of the polymer from Example 1 (10.0 g) was dissolved in methyl acetate (100 mL). The resulting solution was cast uniformly on a Teflon coated plate to provide a liquid film. This was allowed to dry at room temperature for 2 hours to yield a solid film having a thickness of 0.5 mm. The mechanical properties of the film were determined using a MTS Synergie 200 tensile tester. The procured data are summarized in Table I.

TABLE I

Mechanical Properties of a Polyether-ester Film Based on the Polymer of Example 1

| Thickness, mm | 0.5 |
|---|---|
| Peak Stress, MPa | 5.2 |
| Tensile Modulus, MPa | 8.9 |
| Elongation at Break, % | 484 |

EXAMPLE 3

Preparation of a Model Construct of a Typical Bioactive Spray-on Film and Study of Its In Vitro Release Profile In order to prepare the model bioactive construct, fluconazole was mixed into methyl acetate at a 0.5% concentration. Upon dissolution, polyaxial copolyester (PAX-12 from Example 1) was dissolved in the methyl acetate solution by rolling at room temperature for three hours to provide a 10% solution. The drug/polymer solution was sprayed onto a pre-weighed, non-woven polyethylene fabric of known weight per unit area and allowed to dry overnight. The dried piece of the sprayed fabric was weighed to determine loading. The loaded piece was submerged in 10 mL of 7.2 pH phosphate buffer and placed in a 37° C. incubator. At time points of 21, 28, and 48 hours, the buffer was poured off and collected and replaced with 10 mL of fresh buffer. The collected eluent was filtered through 0.45 µtm filters and analyzed by HPLC. The HPLC analysis was done using a C18 column and a gradient method involving acetonitrile and HPLC grade water both containing 0.1% triflouroacetic acid. The release data are summarized in Table I:

TABLE II

Release Data of Fluconazole from the Model Construct

| Time period (Hours) | 21 | 28 | 48 |
|---|---|---|---|
| Drug Released (mg)* | 1.09 | 0.16 | 0.26 |
| Cumulative Percentage of Estimated Total Loading* | 62% | 71% | 86% |

*Initial loading of 1.752 mg/test specimen

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicant hereby discloses all subranges of all ranges disclosed herein. These subranges are also useful in carrying out the present invention.

What is claimed is:

1. An in situ film-forming, sprayable solution comprising at least one absorbable, low crystallinity, segmented copolymer, wherein the at least one absorbable low crystallinity segmented copolymer is selected from the group consisting of polyaxial copolyesters, polyether-esters and polyether-ester-urethanes and exhibits a heat of fusion ($\Delta Hf$) of 1 to 20 J/g, in a methyl acetate and hexadimethyl disiloxane solvent, wherein methyl acetate is a major component of the solvent and hexadimethyl disiloxane is a minor component of the solvent being present less than about 50% by weight, the solution further comprising at least one bioactive agent selected from the group consisting of antimicrobial agents, anesthetic agents, antiviral agents, anti-inflammatory agents, hemostatic agents, and antineoplastic agents.

2. An in situ film-forming, sprayable solution as in claim 1 wherein said solution can be sprayed on animal or human skin and accessible body cavities to form an adherent, flexible, conformable, stretchable, dimensionally stable film having a tack-free outer surface, the film exhibiting an elongation of 100 to 600 percent, a tensile strength of 3-10 MPa and a tensile modulus of 5-20 MPa.

3. An in situ film-forming, sprayable solution as in claim 1 wherein the segmented copolymer comprises from about 0.1 to about 20 weight percent of the solution.

4. An in situ film-forming, sprayable solution as in claim 1 wherein the at least one bioactive agent is from about 0.1 to about 15 weight percent of the absorbable copolymer and comprises a soluble entity or partially soluble micro particles.

5. An in situ film-forming, sprayable solution as in claim 1 wherein the polyaxial copolyester is made from at least two cyclic monomers selected from the group consisting of p-dioxanone, 1,5-dioxapan-2-one, glycolide, 1-lactide, $\epsilon$-caprolactone, trimethylene carbonate and a morpholinedione.

6. An in situ film-forming, sprayable solution as in claim 1 wherein the poly ether-ester is an end-grafted product of a polyethylene glycol and at least one monomer selected from the group of p-dioxanone, 1,5-dioxapan-2-one, glycolide, 1-lactide, $\epsilon$-caprolactone, trimethylene carbonate and a morpholinedione.

7. An in situ film-forming, sprayable solution as in claim 1, wherein the poly ether-ester urethane is an end-grafted product of a polyethylene glycol and at least one monomer selected from the group consisting of p-dioxanone, 1,5-dioxapan-2-one, glycolide, 1-lactide, $\epsilon$-caprolactone, trimethylene carbonate and a morpholinedione, the end-grafted product is further interlinked with an aliphatic diisocyanate selected from the group consisting of 1,4-butane, 1,6-hexane, and a lysine diisocyanate.

8. An in situ film-forming, sprayable solution as in claim 4 wherein the at least one bioactive agent is selected from the group consisting of miconazole, ketoconazole, metronidazole, curcumin, capsaicin, lidocaine, benzocaine, 8-hydroxyquinaline, triclosan, and paclitaxel.

9. An in situ film-forming, sprayable solution as in claim 1 for treating or preventing at least one malady selected from fungal infection, bacterial infection, viral infection, pain, and bleeding.

* * * * *